US00PP27729P3

(12) United States Plant Patent
Van Dijk

(10) Patent No.: US PP27,729 P3
(45) Date of Patent: Feb. 28, 2017

(54) ***ANTHURIUM* PLANT NAMED 'ANTHDOXIL'**

(50) Latin Name: ***Anthurium andreanum* L.**
Varietal Denomination: ANTHDOXIL

(71) Applicant: ANTHURA B.V., Bleiswijk (NL)

(72) Inventor: Jan Van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 99 days.

(21) Appl. No.: 14/544,918

(22) Filed: Mar. 5, 2015

(65) Prior Publication Data

US 2016/0270281 P1 Sep. 15, 2016

(51) Int. Cl.
*A01H 5/02* (2006.01)

(52) U.S. Cl.
USPC ..... Plt./365

(58) Field of Classification Search
USPC ..... Plt./365
See application file for complete search history.

(56) References Cited

PUBLICATIONS

Anthura Unlimited in Varieties 2014, *Anthurium* Cut flower & Pot plant culture, pp. 40 and 47-48.*

Information Disclosure Statement for U.S. Appl. No. 14/544,292, filed Jun. 14, 2016, one page.*

Pluto Plant Variety Database Jul. 23, 2016, retrived on Jul. 26, 2016, retrieved from the Internet at <https://www3.wipo.int/pluto/user/en/index.jsp> one page.*

Anthura *Anthurium*: Cut flower and pot plant culture, published Nov. 2014, pp. 1-3, 40, 47.

EU Community Plant Variety Rights Application No. 2013/1858, Application No. A201300726, filed Jul. 5, 2013, 7 pages.

EU Community Plant Variety Office Official Gazette, 5.2013, Oct. 15, 2013, pp. 1, 28, 48, 2 introductory pages.

EU Community Plant Variety Rights Grant No. EU 41007, issued May 26, 2015, 2 pages.

* cited by examiner

*Primary Examiner* — June Hwu

(74) *Attorney, Agent, or Firm* — Jondle & Associates, P.C.

(57) ABSTRACT

A new and distinct variety of *Anthurium* plant named 'ANTHDOXIL' particularly characterized by having bright, shiny, orange, cordate spathes, white spadix with yellow tips, a high and more spreading plant habit and light green foliage, is disclosed.

3 Drawing Sheets

Genus and species: *Anthurium andreanum* L.
Variety denomination: 'ANTHDOXIL'.

BACKGROUND OF THE NEW PLANT

The present invention comprises a new and distinct variety of *Anthurium*, botanically known as *Anthurium andreanum* L., and hereinafter referred to by the variety name 'ANTHDOXIL'. The new variety originated from a hybridization made in February 2005 in Bleiswijk, The Netherlands. The female parent is a red Anthurium pot plant designated '5432-12' (unpatented), and the male parent was a red *Anthurium* plant designated '5089-02' (unpatented).

A single plant was selected in February 2007 and has been asexually reproduced repeatedly by meristem tissue culture in Bleiswijk, The Netherlands over a five-year period. The present invention has been found to retain its distinctive characteristics through successive asexual propagations.

Plant Breeder's Rights for this variety have been applied for in Europe on Jul. 5, 2013. 'ANTHDOXIL' has not been made publicly available or sold anywhere in the world more than one year prior to the filing of this application.

SUMMARY OF THE INVENTION

The following are the most outstanding and distinguishing characteristics of this new variety when grown under normal horticultural practices in Bleiswijk, The Netherlands.

1) Bright, shiny, orange, cordate spathe;
2) White spadix with yellow tip;
3) A high and more spreading plant habit; and
4) Light green foliage.

DESCRIPTION OF THE PHOTOGRAPHS

This new *Anthurium* plant is illustrated by the accompanying photographs which show the overall plant habit including blooms, buds and foliage of the plant; the colors shown are as true as can be reasonably obtained by conventional photographic procedures. The photographs are of a 25-week old plant grown in a greenhouse in Bleiswijk, The Netherlands in February 2015.

DESCRIPTION OF THE NEW VARIETY

Figure 1:
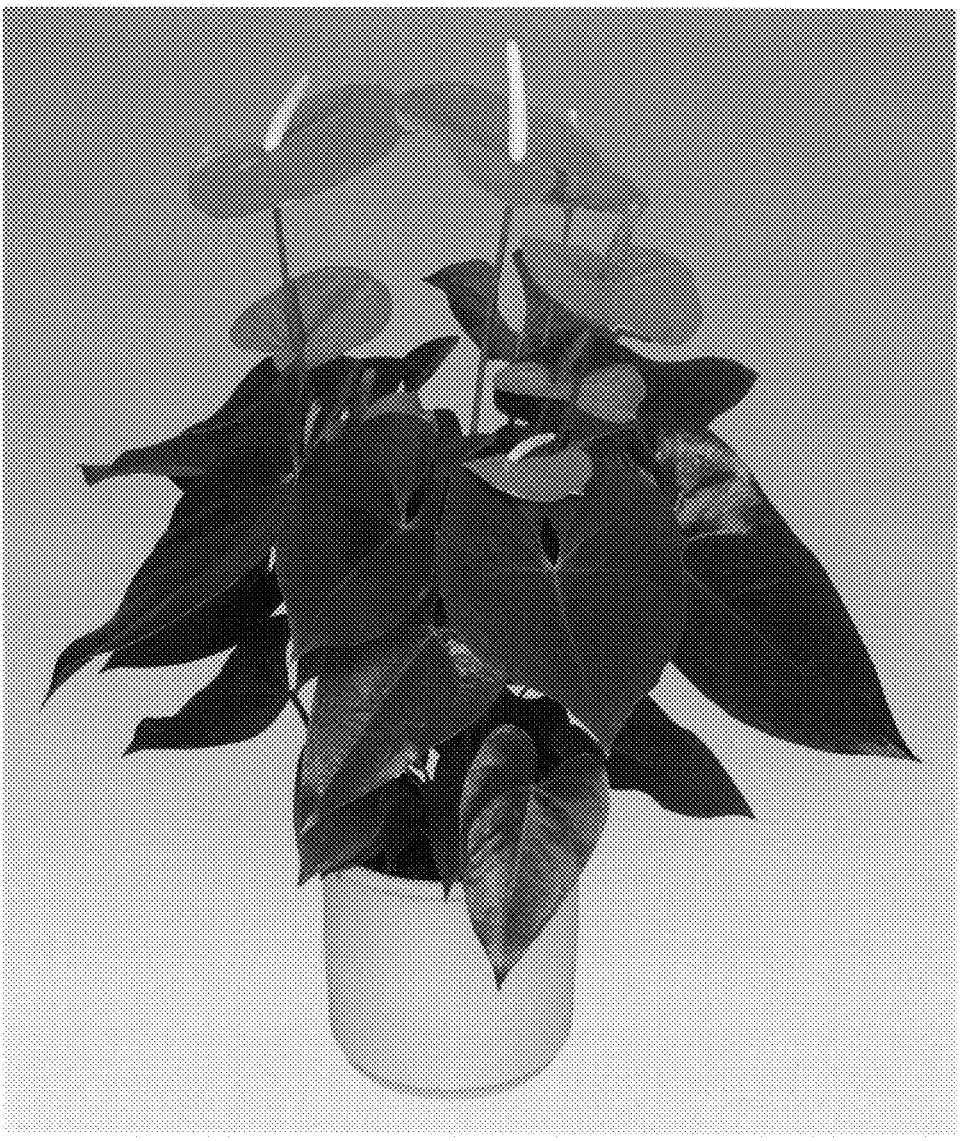
FIG. 1 shows the overall plant habit, including blooms, buds and foliage.
Figure 2:
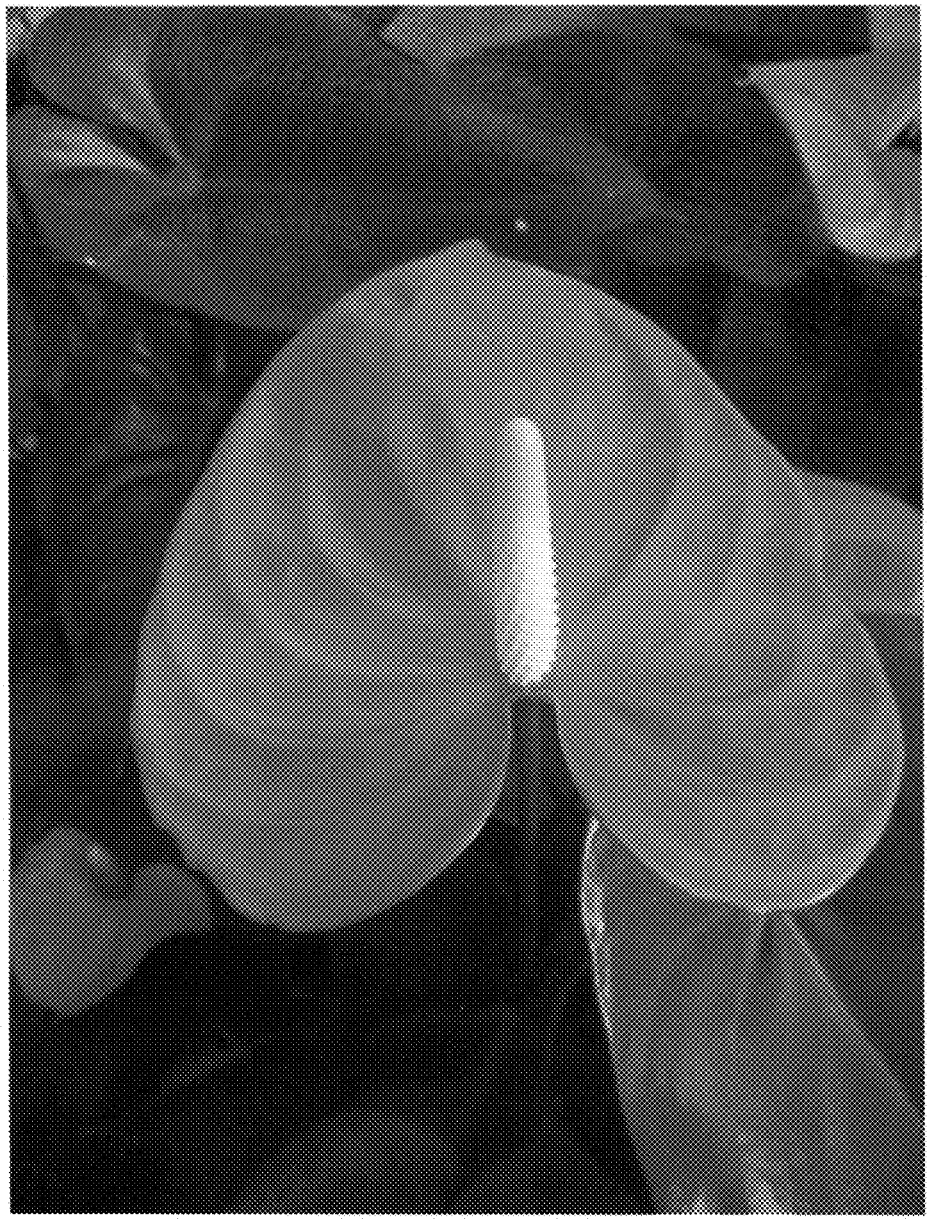
FIG. 2 shows a close-up of the mature spathe.
Figure 3:
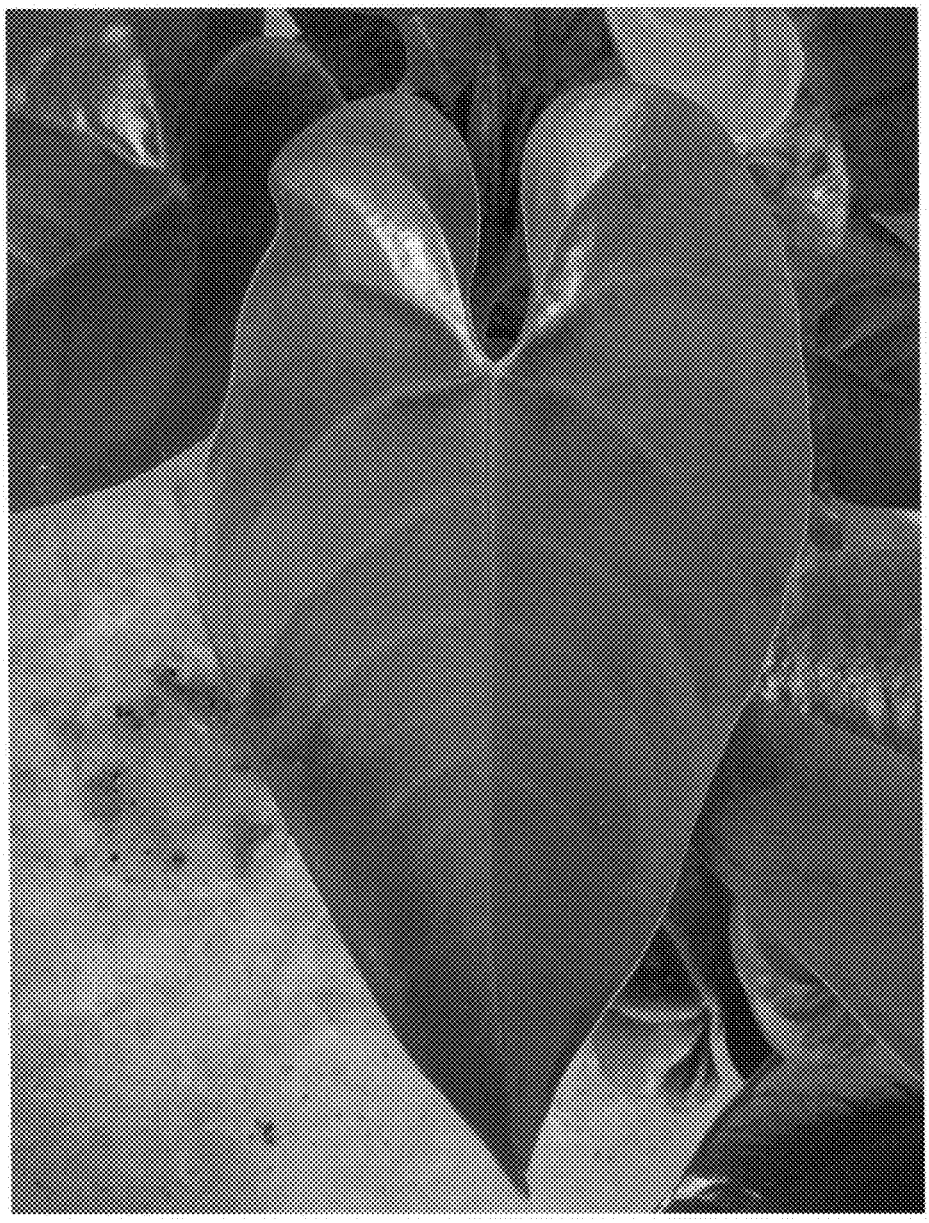
FIG. 3 shows the upper leaf surface.

The following detailed description sets forth the distinctive characteristics of 'ANTHDOXIL'. The data which define these characteristics were collected from asexual reproductions carried out in Bleiswijk, The Netherlands. The plant history was taken on 25-week old plants which were planted from tissue culture in 17-centimeter pots and grown in a glass greenhouse between 19° C. and 24° C. Observations were made in February 2015. Color readings were taken under 5000 lux natural light in the greenhouse. Color references are primarily to The R.H.S. Colour Chart of The Royal Horticultural Society of London (R.H.S.) (2001).

DETAILED BOTANICAL DESCRIPTION

Classification:

*Family*.—Araceae.

*Botanical*.—*Anthurium andreanum* L.

*Common name*.—*Anthurium*.

*Demonimation*.—'ANTHDOXIL'.

Parentage:

*Female parent*.—*Anthurium* plant '5432-12' (unpatented).

*Male parent*.—*Anthurium* plant '5089-02' (unpatented).

Plant:

*Propagation*.—Tissue culture.

*Root description*.—Fleshy white-cream colored roots with small hairy lateral roots having yellow-colored root tips.

*Time to produce a finished flowering plant*.—35 to 40 weeks for a 17 cm pot.

*Growth habit*.—Herbaceous perennial.

*Height* (*measured from soil, including inflorescence*) .—50.0 cm to 60.0 cm.

*Width* (*measured from leaf tips*).—50.0 cm to 55.0 cm.

Leaves:

*Immature leaves*.—Length: 15.0 cm to 25.0 cm. Width: 9.0 cm to 13.0 cm. Color: Upper surface: RHS 146A. Lower surface: RHS 152A. Texture (both upper and lower surfaces): Shiny.

*Mature leaves*.—Length (fully expanded): 22.0 cm to 28.0 cm. Width: 12.0 cm to 15.0 cm. Shape: Ovate. Apex: Acuminate. Base: Cordate. Leaf blade angle with the petiole: Between 100 degrees and 120 degrees. Leaf margin: Entire. Color: Upper surface: RHS 137A. Lower surface: RHS 137C. Texture: Shiny, leathery and thick. Venation: Pinnate veining; the mid-vein and primary veins (the veins that radiate out from the junction of petiole and leaf) protrude at the underside of the leaf blade. Venation color: Upper surface: RHS 146B. Lower surface: RHS 146C.

*Lobes*.—Arrangement: Leaf blade has two lobes extending past the petiole. The lobes are non-touching. Length of lobes of mature leaf blades: 4.0 cm to 6.5 cm. Width of lobes of mature leaf blades: 5.0 cm to 6.0 cm. Distance from petiole/leaf junction to highest point on lobes of mature leaf blades: 2.0 cm to 4.0 cm.

*Petiole*.—Cross-section: Round. Diameter: 0.3 cm to 0.4 cm. Length: 25.0 cm to 30.0 cm for a mature leaf size. Color: Mature leaf: RHS 146B. Immature leaf: RHS 152B. Cataphyl color surrounding the petiole: Outside: RHS 48B (with a touch of green). Inside: RHS 48D (with a touch of green).

*Geniculum*.—Length: 2.0 cm to 2.5 cm. Width: 0.4 cm to 0.5 cm. Color: RHS 176B (with a touch of green).

Inflorescence:

*Arrangement*.—Single.

*Flowering habit* (*length of flowering season*).—Continuous.

*Number of inflorescences per plant*.—4 to 6.

*Fragrance*.—Absent.

*Longevity of inflorescence on plant*.—Over a year.

*Longevity of the flower as a cut flower*.—35 to 45 days.

Spathe:

*Buds*.—The spathe is tightly rolled around the spadix and extrudes from the peduncle sheath. After the spathe is fully open the peduncle elongates some extra centimeters.

*Arrangement*.—Spathe angle with the peduncle is between 100 degrees and 120 degrees; the spathe stands on a wiry peduncle about 4.0 cm to 6.0 cm above the foliage.

*Lobe position*.—Free.

*Shape*.—Cordate.

*Apex*.—Broad acuminate.

*Base*.—Cordate.

*Texture*.—Shiny and slightly blistered.

*Margin*.—Entire.

*Size*.—Height: 36.0 cm to 42.0 cm (peduncle length at maturity). Length: 10.5 cm to 12.5 cm. Width: 8.5 cm to 10.5 cm.

*Color*.—Just fully open: Upper surface: RHS 44B. Lower surface: RHS 44C. This orange-red color remains approximately 35 to 40 weeks after opening. After this period the spathe is limp and dies.

Peduncle:

*Shape*.—Erect.

*Cross-section*.—Round.

*Length*.—36.0 cm to 42.0 cm.

*Diameter*.—0.3 cm to 0.4 cm.

*Color*.—RHS 146C at unrolling of spathe, slowly turning RHS 177A when the spathe matures.

Flowering time:

*General*.—One small rooted untreated tissue culture plant of 8.0 cm tall will flower after 4 to 6 months, depending on the season, and 4 to 6 blossoms will appear. More blossoms appear after some additional weeks so that a full flowering and commercial plant will have 7 to 9 orange-red spathes. Smaller blossoms may occur on less mature plants.

Spadix:

*Size*.—Length: 3.5 cm to 5.5 cm (depending on flower size). Width (at apex): 0.4 cm to 0.5 cm. Width (at base): 0.6 cm to 0.8 cm.

*Shape*.—Columnar.

*Angle from spadix tip to peduncle*.—170 to 180 degrees (spadix is almost in one line with peduncle).

*Texture*.—When the spathe is unfurling the spadix is smooth. When the spadix matures, small stigmata protrude. The stigmata are evenly distributed round the spadix. The spadix matures from base to top, slowly giving the spadix a somewhat rough appearance.

*Color*.—Immature: RHS 14C. Mature: RHS 158C. Ages to: RHS 144A.

Flowers:

*Quantity per spadix*.—240 to 260.

*Spadix flower arrangement*.—Bisexual, rounded in cross-section.

*Shape*.—Rounded.

*Size*.—Length: 0.05 cm to 0.1 cm. Diameter (maximum): 0.1 cm.
*Color*.—RHS 158C.
Reproductive organs:
*Stamens*.—Not visible.
*Pollen amount*.—Very few.
*Pollen color*.—RHS 156D.
*Pistil*.—Quantity: Many. Length: Less than 0.01 cm. Color: RHS 156D.
*Style*.—Not observed.
*Stigma*.—Shape: Ovoid. Diameter: Less than 0.01 cm. Color: RHS 158C.
*Ovary*.—Rarely visible.
*Ovary color*.—Not measured.
Fruit and seed set: None observed.
Disease and pest resistance: Not observed to date.

COMPARISON WITH PARENTAL AND COMMERCIAL VARIETIES

'ANTHDOXIL' differs from the female parent plant '5432-12' (unpatented) in that 'ANTHDOXIL' has an orange-red spathe, whereas '5432-12' has a red spathe.

'ANTHDOXIL' differs from male parent plant '5089-02' (unpatented) in that 'ANTHDOXIL' has a white spadix and an orange-red spathe, whereas '5089-02' has a pink spadix and a red spathe.

'ANTHDOXIL' differs from commercial variety 'ANTHCANDOL' (unpatented) in that 'ANTHDOXIL' has a bright green leaf blade and slight spathe blistering, whereas 'ANTHCANDOL' has a more dark green leaf blade and intermediate spathe blistering.

'ANTHDOXIL' differs from commercial variety 'ANTHSELAP' (unpatented) in that 'ANTHDOXIL' has a less blistered spathe than 'ANTHSELAP'.

I claim:

1. A new and distinct variety of *Anthurium* plant named 'ANTHDOXIL', substantially as illustrated and described herein.

* * * * *